United States Patent [19]

Costantini et al.

[11] Patent Number: 4,560,801

[45] Date of Patent: Dec. 24, 1985

[54] PROCESS FOR THE PREPARATION OF 4-HYDROXY-2,4,6-TRIMETHYL-2,5-CYCLOHEXADIENONE

[75] Inventors: Michel Costantini, Lyon; Francoise Igersheim, Villeurbanne; Léon Krumenacker, Serezin Du Rhone, all of France

[73] Assignee: Rhone-Poulenc Sante, Courbevoie, France

[21] Appl. No.: 629,423

[22] Filed: Jul. 10, 1984

[30] Foreign Application Priority Data

Jul. 13, 1983 [FR] France .............................. 83 11708

[51] Int. Cl.$^4$ .............................................. C07C 45/30
[52] U.S. Cl. ................................................... 568/362
[58] Field of Search ......................................... 568/362

[56] References Cited

U.S. PATENT DOCUMENTS

| | | | |
|---|---|---|---|
| 2,662,918 | 12/1953 | Spaulding | 568/362 |
| 2,843,606 | 7/1958 | Pennino | 568/362 |
| 2,903,487 | 9/1959 | Coffield | 568/362 |
| 3,895,069 | 7/1975 | Atkinson et al. | 568/362 |
| 3,928,453 | 12/1975 | Atkinson | 568/362 |
| 4,477,682 | 10/1984 | Tomita et al. | 568/362 |

FOREIGN PATENT DOCUMENTS

2019196  4/1969  Fed. Rep. of Germany ...... 568/362

OTHER PUBLICATIONS

Fieser et al., "Reagents for Organic Synthesis", pp. 487–489, John Wiley & Sons, Inc., (1973).
Can. J. Chem., Alfred Fischer and George N. Henderson, "IPSO Chlorination of 4-Alkylphenols. Formation of 4-Alkyl-Chlorocyclohexa-2-5-Dienones", pp. 552–557.
Acta Chemica Scandinavica B 36 (1982) 675–683, Karl Erik Berquist, Anders Nilsson and Alvin Ronlan, "Electrophilic Chlorination of 4-Methylphenols with Molecular Chlorine", etc.

*Primary Examiner*—James H. Reamer
*Attorney, Agent, or Firm*—Stevens, Davis, Miller & Mosher

[57] ABSTRACT

4-Hydroxy-2,4,6-trimethyl-2,5-cyclohexadienone is prepared by treatment of 2,4,6-trimethylphenol with a halogenation agent and water in the presence of an organic solvent which is inert to the halogenation agent.

4 Claims, No Drawings

PROCESS FOR THE PREPARATION OF 4-HYDROXY-2,4,6-TRIMETHYL-2,5-CYCLOHEXADIENONE

The present invention relates to the preparation of 4-hydroxy-2,4,6-trimethyl-2,5-cyclohexadienone, which is an intermediate for the synthesis of trimethylhydroquinone (TMHQ) which is itself a precursor of vitamin E.

It is known that 4-hydroxy-2,4,6-trimethyl-2,5-cyclohexadienone can be prepared by oxidation of 2,4,6-trimethylphenol, for example with a peracid or with molecular oxygen in basic medium. However, to perform the oxidation in air at a pressure in the region of 100 bars involves technical difficulties related to considerable problems of safety.

According to the process described by A. Nilsson et al., Tetrahedron Letters, 1107 (1975), a 4-hydroxy-2,5-cyclohexadienone can also be obtained by solvolysis of a 4-chloro-2,5-cyclohexadienone in the presence of water and a silver salt, 4-chloro-2,5-cyclohexadienone being obtainable by the action of a chlorination agent, such as gaseous chlorine in an organic solvent such as dichloromethane or dimethylformamide according to K. E. Bergquist et al., Acta Chimica Scandinavia, B 36, 675 (1982), or by the action of chlorine in acetic anhydride according to A. Fischer and G. N. Henderson, Can. J. Chem., 57, 552 (1979), on a 4-alkylphenol and, more particularly, on 2,4,6-trimethylphenol.

The action of chlorine on 2,4,6-trimethylphenol either leads to a mixture of 4-chloro-2,4,6-trimethyl-2,5-cyclohexadienone and 3-chloro-2,4,6-trimethylphenol, or else requires the use of a costly solvent such as acetic anhydride for good yields to be obtained.

Furthermore, the known conversion of 4-chloro-2,4,6-trimethyl-2,5-cyclohexadienone to 4-hydroxy-2,4,6-trimethyl-2,5-cyclohexadienone requires the use of a silver salt, which makes the process difficult to use industrially.

It has now been found, and this forms the subject of the present invention, that the preparation of 4-hydroxy-2,4,6-trimethyl-2,5-cyclohexadienone can be considerably improved by reacting a halogenation agent and water with the 2,4,6-trimethylphenol in an organic solvent which is inert with respect to the halogenation agent.

According to the conditions used, the conversion of 2,4,6-trimethylphenol to 4-hydroxy-2,4,6-trimethyl-2,5-cyclohexadienone can be carried out in a single stage, the halogenation and hydrolysis being performed simultaneously; or alternatively, in two stages, the halogenation product being hydrolysed subsequently.

When the process is carried out in two stages, the halogenation can be performed in an anhydrous medium.

The following are particularly suitable as halogenation agents: the molecular halogens (especially chlorine), sulphuryl chloride, and any other means capable of generating chlorine in situ.

A molar ratio of halogenation agent/2,4,6-trimethylphenol of between 0.5 and 2, and preferably between 0.8 and 1.2, is generally used.

As solvents, there can be used aliphatic of cycloaliphatic hydrocarbons which are optionally halogenated (hexane, methyl cyclohexane, carbon tetrachloride, chloroform, methylene chloride, dichloro- and trichloroethane, chlorine-containing and fluorine-containing solvents), ethers (methyl butyl ether, dioxane, tetrahydrofuran), aliphatic carboxylic acids (acetic acid), organic esters of aliphatic acids or phosphoric acid (ethyl acetate, triethyl phosphate, tributyl phosphate), amides (dimethylformamide, N-methylpyrrolidone) or mixtures of these.

The halogenation is generally performed at a temperature between $-0°$ C. and the boiling point of the reaction mixture.

The concentration of 2,4,6-trimethylphenol in the solvent is generally between 1% and the saturation value for 2,4,6-trimethylphenol in the solvent in question. Preferably, the concentration is between 5 and 15% (weight/volume).

The halogenation phase can be carried out in an ether or an amide, possibly together with an aliphatic or cycloaliphatic hydrocarbon which is optionally halogenated, a carboxylic acid or an aliphatic carboxylic acid ester or a phosphoric acid ester, or alternatively in an aliphatic or cycloaliphatic hydrocarbon which is optionally halogenated, an ether, an aliphatic carboxylic acid, an aliphatic carboxylic acid ester or a phosphoric acid ester or an amide in the presence of an inorganic or organic base.

An inorganic or organic base is generally used, which is either soluble or insoluble in the chosen solvent. The molar ratio of the basic agent to the halogenation agent is between 1 and 10, and preferably between 1 and 2. However, the halogenation takes place with satisfactory results when 1 mole of basic agent is used per mole of halogenation agent.

The bases which are particularly suitable are chosen from among the inorganic bases (caustic soda, caustic potash, lithia, sodium bicarbonate and carbonate, potassium bicarbonate and carbonate, lime, calcium carbonate, sodium acetate and potassium acetate) or organic bases (amine, pyridine, substituted pyridines).

The chlorination is preferably performed by bubbling gaseous chlorine into a stirred solution of 2,4,6-trimethylphenol in the organic solvent possibly in the presence of an inorganic or organic base, the base being usable in excess relative to the 2,4,6-trimethylphenol present.

The chlorination is generally carried out at a temperature between 0° C. and the boiling point of the reaction mixture.

Whatever the method of halogenation used, the 4-hydroxy-2,4,6-trimethyl-2,5-cyclohexadienone is obtained by treating the halogenation product with water at a pH of between 10 and 0 and preferably between 9 and 0. The pH of the reaction medium can possibly be adjusted by the addition of a base.

It is possible to add the water to the reaction mixture after removal, if necessary, of the insoluble base by filtration. However, it is also possible to isolate the halogenation product from the reaction mixture after possible filtration and after evaporation of the solvent, and to purify it if required. In either case, the hydrolysis is carried out by stirring the crude product thus obtained suspended in water, possibly in the presence of a base.

Whichever product the hydrolysis is performed on, whether the product in the reaction mixture, the crude product or the purified product, the hydrolysis is effected by water at a temperature generally between 0° C. and the boiling point of the reaction mixture.

The hydrolysis can be performed in heterogeneous medium when the solvent and water are only slightly miscible, or in homogeneous phase when the solvent and water are miscible or when a solvent intended for homogenisation of the reaction medium is added to an immiscible mixture of solvent and water.

When the process according to the invention is carried out in a single stage, the conversion of the 2,4,6-trimethylphenol to 4-hydroxy-2,4,6-trimethyl-2,5-cyclohexadienone can be carried out in either homogeneous or heterogeneous medium.

Simultaneous halogenation and hydrolysis are carried out by treating 2,4,6-trimethylphenol with a halogenation agent in solution in an organic solvent in the presence of a sufficient quantity of water, i.e., at least one mole of water per mole of 2,4,6-trimethylphenol present, possibly in the presence of an inorganic or organic base so that the pH of the reaction mixture is between 10 and 0 and preferably between 9 and 0.

As halogenation agents, those which are generally used for halogenation in anhydrous medium, can be used, employing the same molar ratios as those indicated above.

When proceeding according to one or other of the variants of the process according to the invention, the conversion ratio of the 2,4,6-trimethylphenol is generally greater than 80%, and the yield of 4-hydroxy-2,4,6-trimethyl-2,5-cyclohexadienone is generally greater than 60%.

Another subject of the invention relates to the process for isolation of 4-hydroxy-2,4,6-trimethyl-2,5-cyclohexadienone. When the procedure is carried out in the presence of a solvent not miscible with water, the 4-hydroxy-2,4,6-trimethyl-2,5-cyclohexadienone can be isolated by extraction of the organic phase containing the 4-hydroxy-2,4,6-trimethyl-2,5-cyclohexadienone with water, followed by evaporation of the aqueous phase or extraction of the aqueous solution with an immiscible organic solvent, which need only be evaporated subsequently.

4-hydroxy-2,4,6-trimethyl-2,5-cyclohexadienone can be converted to trimethylhydroquinone under the conditions described in French Pat. No. 73/33,374 published under the number 2,200,225, i.e. by heating the former compound to a temperature of at least 100° C. in a non-acidic liquid medium such as methanol and an aqueous medium.

The examples which follow illustrate the invention.

EXAMPLE 1

The following are introduced into a 250 cc cylindrical reaction vessel, incorporating central stirring, a descending tube for admission of chlorine, a reflux condenser, a thermometer and a system of temperature regulation:

| | |
|---|---|
| 2,4,6-trimethylphenol | 10.9 g (80 mmoles) |
| carbon tetrachloride | 160 cc |
| sodium bicarbonate | 10.55 g (120.8 mmoles) |

The reaction mixture is stirred at a speed of 1,000 rpm, and maintained at 0° C. while passing in a stream of gaseous chlorine at the flow rate of 5 liters/hour during 21 minutes (equivalent to 78.1 mmoles of chlorine).

After filtration, the reaction mixture is poured into a stirred reaction vessel containing water (1 liter) and sodium bicarbonate (6.7 g, equivalent to 80 mmoles). After 2 hours' stirring at a temperature close to 20° C., the reaction mixture is decanted and the aqueous phase extracted with isopropyl ether (2×500 cc). The organic phases thus obtained are combined. Gas-liquid chromatography is used for determination of the residual 2,4,6-trimethylphenol, and of the 4-hydroxy-2,4,6-trimethyl-2,5-cyclohexadienone and 3-chloro-2,4,6-trimethylphenol formed. The following results are obtained:
conversion ratio of 2,4,6-trimethylphenol: 88.5%
molar yield of 4-hydroxy-2,4,6-trimethyl-2,5-cyclohexadienone relative to the 2,4,6-trimethylphenol converted: 70%
yield of 3-chloro-2,4,6-trimethylphenol: 10%.

By way of comparison, when the procedure is carried out under the conditions described above but in the absence of sodium bicarbonate, the following results are obtained:
conversion ratio of 2,4,6-trimethylphenol: 84%
yield of 3-chloro-2,4,6-trimethylphenol: in the region of 80%
yield of 4-hydroxy-2,4,6-trimethyl-2,5-cyclohexadienone: trace.

EXAMPLE 2

The procedure is as in Example 1, replacing the sodium bicarbonate by dimethylformamide (98 mmoles). The following results are obtained:
conversion ratio of 2,4,6-trimethylphenol: 74.5%
yield of 4-hydroxy-2,4,6-trimethyl-2,5-cyclohexadienone: 62%.

EXAMPLE 3

The procedure is as in Example 1, replacing the sodium bicarbonate by pyridine (82 mmoles). The following results are obtained:
conversion ratio of 2,4,6-trimethylphenol: 88%
yield of 4-hydroxy-2,4,6-trimethyl-2,5-cyclohexadienone: 38%.

EXAMPLE 4

The procedure is as in Example 1, replacing the sodium bicarbonate by triethylamine (82 mmoles). The following results are obtained:
conversion ratio of 2,4,6-trimethylphenol: 74%
yield of 4-hydroxy-2,4,6-trimethyl-2,5-cyclohexadienone: 49%.

EXAMPLE 5

The procedure is as in Example 1, replacing the carbon tetrachloride by methylene chloride, and sodium bicarbonate (121 mmoles) being present. The following results are obtained:
conversion ratio of 2,4,6-trimethylphenol: 80.5%
yield of 4-hydroxy-2,4,6-trimethyl-2,5-cyclohexadienone: 68%.

EXAMPLE 6

The procedure is as in Example 1, replacing the carbon tetrachloride by dimethylformamide without adding sodium bicarbonate. The following results are obtained:
conversion ratio of 2,4,6-trimethylphenol: 80.5%
yield of 4-hydroxy-2,4,6-trimethyl-2,5-cyclohexadienone: 50.5%.

EXAMPLE 7

The procedure is as in Example 1, using the following quantities of products:

| | |
|---|---|
| 2,4,6-trimethylphenol | 21.8 g (160 mmoles) |
| carbon tetrachloride | 160 cc |
| sodium bicarbonate | 21.1 g (241.6 mmoles) |

The stream of gaseous chlorine is passed into the reaction mixture at a flow rate of 5 liters/hour in the course of 42 minutes (equivalent to 156.2 mmoles of chlorine), the reaction mixture being maintained at 0° C. and stirred at a speed of 1,000 rpm.

After filtration, the reaction mixture is poured into a stirred reaction vessel containing water (2 liters) and sodium bicarbonate (13.4 g, equivalent to 160 mmoles). After 2 hours' stirring at a temperature close to 20° C., the reaction mixture is treated under the conditions of Example 1. The following results are obtained:
conversion ratio of 2,4,6-trimethylphenol: 81.5%
yield of 4-hydroxy-2,4,6-trimethyl-2,5-cyclohexadienone: 59%.

EXAMPLE 8

The procedure is as in Example 1, but using only 70.4 mmoles of chlorine. The following results are obtained:
conversion ratio of 2,4,6-trimethylphenol: 78.5%
yield of 4-hydroxy-2,4,6-trimethyl-2,5-cyclohexadienone: 69.5%.

EXAMPLE 9

The following are introduced into a cylindrical reaction vessel incorporating central stirring, a descending tube for admission of chlorine, a reflux condenser, a thermometer and a system of temperature regulation:

| | |
|---|---|
| 2,4,6-trimethylphenol | 13.6 g (100 mmoles) |
| carbon tetrachloride | 200 cc |
| sodium bicarbonate | 16.8 g (200 mmoles) |

Speed of stirring is 1,000 rpm. With the reaction mixture maintained at 0° C., a stream of gaseous chlorine is passed in at a flow rate of 5 liters/hour in the course of 26 minutes (equivalent to 96.7 mmoles of chlorine).

The temperature is allowed to rise to 20° C., and water (200 cc) is added rapidly. The stirring is then continued for 2 hours. After decantation, the aqueous layer is extracted with isopropyl ether (4×50 cc).

In the phase containing the carbon tetrachloride, the following are determined by gas-liquid chromatography:
2,4,6-trimethylphenol: 1.78 g (13.06 mmoles)
4-hydroxy-2,4,6-trimethyl-2,5-cyclohexadienone: 8.44 g (55.5 mmoles).

In the ether phase, the following are determined by gas-liquid chromatography:
2,4,6-trimethylphenol: 0%
4-hydroxy-2,4,6-trimethyl-2,5-cyclohexadienone: 1.61 g (10.6 mmoles).
The overall balance is as follows:
conversion ratio of 2,4,6-trimethylphenol: 86.9%
yield of 4-hydroxy-2,4,6-trimethyl-2,5-cyclohexadienone: 76%.

EXAMPLE 10

The procedure is carried out under the same conditions as in Example 9, introducing the following quantities:

| | |
|---|---|
| 2,4,6-trimethylphenol | 13.6 g (0.1 mole) |
| carbon tetrachloride | 200 cc |
| sodium bicarbonate | 16.8 g (0.2 mole) |

Gaseous chlorine (0.098 mole) is passed into the stirred reaction mixture, which is maintained at 25° C. Water (200 cc) is then added, and the reaction mixture is then stirred for 2½ hours at 25° C. The aqueous phase, after separation by decantation, is extracted with isopropyl ether. The organic phases are combined. Analysis of the organic phase by gas-liquid chromatography shows that:
the conversion ratio of 2,4,6-trimethylphenol is 88%
the yield of 4-hydroxy-2,4,6-trimethyl-2,5-cyclohexadienone is 71.5%.

EXAMPLE 11

The procedure is as in Example 1, using the following products:

| | |
|---|---|
| 2,4,6-trimethylphenol | 10.9 g (80 mmoles) |
| carbon tetrachloride | 160 cc |
| sodium bicarbonate | 10.55 g (120.8 mmoles). |

Gaseous chlorine (78 mmoles) is passed, in the course of 21 minutes, into the stirred reaction mixture, which is maintained at 0° C. After filtration, the reaction mixture is poured into a reaction vessel containing a water-tetrahydrofuran mixture (20:80 by volume, 1,000 cc) and sodium bicarbonate (9.2 g). The homogeneous mixture is stirred for 2 hours at a temperature close to 25° C. The carbon tetrachloride and tetrahydrofuran are removed by distillation under reduced pressure, and the aqueous phase is then extracted with isopropyl ether. Analysis of the organic phase shows that:
the conversion ratio of 2,4,6-trimethylphenol is 84%
the yield of 4-hydroxy-2,4,6-trimethyl-2,5-cyclohexadienone is 66%.

EXAMPLE 12

The procedure is carried out in the same apparatus as that used in Example 9, introducing the following quantities:

| | |
|---|---|
| 2,4,6-trimethylphenol | 13.6 g (0.1 mole) |
| carbon tetrachloride | 200 cc |
| sodium carbonate | 10.6 g (0.1 mole). |

Gaseous chlorine (0.098 mole) is passed into the stirred reaction mixture, which is maintained at 0° C., and the temperature is then allowed to rise to about 20° C. Water (200 cc) is then added, and the reaction mixture is then stirred for 2½ hours at a temperature close to 20° C. After separation by decantation, the aqueous phase is extracted with isopropyl ether. The organic phases are combined. Analysis of the organic phase by gas-liquid chromatography shows that:
the conversion ratio of 2,4,6-trimethylphenol is 83%
the yield of 4-hydroxy-2,4,6-trimethyl-2,5-cyclohexadienone is 77.5%.

EXAMPLE 13

The procedure is as in Example 12, replacing the sodium carbonate (0.1 mole) by caustic soda (0.1 mole). The following results are obtained:

conversion ratio of 2,4,6-trimethylphenol: 81.3%
yield of 4-hydroxy-2,4,6-trimethyl-2,5-cyclohexadienone: 65%.

EXAMPLE 14

The procedure is carried out in the same apparatus as that used in Example 9, introducing the following quantities:

| | |
|---|---|
| 2,4,6-trimethylphenol | 13.6 g (0.1 mole) |
| carbon tetrachloride | 200 cc |
| sodium bicarbonate | 8.4 g (0.1 mole) |

Gaseous chlorine (0.098 mole) is passed into the stirred reaction mixture, which is maintained at 0° C. After the reaction mixture has returned to a temperature close to 20° C., water (200 cc) is added, and the mixture is then stirred for 2½ hours.

The aqueous phase is separated by decantation, and is then extracted with isopropyl ether. The organic phases are combined. Analysis of the organic phase by gas-liquid chromatography shows that:
the conversion ratio of 2,4,6-trimethylphenol is 75.9%
the yield of 4-hydroxy-2,4,6-trimethyl-2,5-cyclohexadienone is 72.5%.

EXAMPLE 15

The procedure is carried out in the same apparatus as that used in Example 9. The following are introduced:

| | |
|---|---|
| carbon tetrachloride | 200 cc |
| water | 200 cc |
| 2,4,6-trimethylphenol | 13.6 g (0.1 mole) |
| sodium bicarbonate | 16.8 g (0.2 mole) |

The initial pH of the mixture is equal to 8. The reaction mixture is cooled to 0° C., and chlorine (0.098 mole) is then passed in, in the course of 24 minutes. The temperature is then allowed to rise to about 20° C. Stirring is continued for 2½ hours at this temperature. After extraction under the usual conditions, analysis of the organic phase by gas-liquid chromatography shows that:
the conversion ratio of 2,4,6-trimethylphenol is 81.3%
the yield of 4-hydroxy-2,4,6-trimethyl-2,5-cyclohexadienone is 77%.

EXAMPLE 16

The procedure is carried out in the same apparatus as that used in Example 9. The following are introduced:

| | |
|---|---|
| carbon tetrachloride | 200 cc |
| water | 200 cc |
| 2,4,6-trimethylphenol 13.6 | g (0.1 mole). |

Chlorine (0.098 mole) is passed, in the course of 24 minutes, into the stirred reaction mixture, which has been cooled to 0° C. The temperature is allowed to rise to about 20° C., and stirring is continued for 2½ hours. After extraction under the usual conditions, analysis of the organic phase by gas-liquid chromatography shows that:
the conversion ratio of 2,4,6-trimethylphenol is 73.4%
the yield of 4-hydroxy-2,4,6-trimethyl-2,5-cyclohexadienone is 66.8%.

EXAMPLE 17

A carbon tetrachloride-containing phase, obtained from the chlorination of 2,4,6-trimethylphenol, is used, the analysis of which gives the following composition:

| | |
|---|---|
| carbon tetrachloride | 1,400 g |
| 2,4,6-trimethylphenol | 11.5 g |
| 4-hydroxy-2,4,6-trimethyl-2,5-cyclohexadienone | 33.5 g. |

The carbon tetrachloride-containing phase is extracted with distilled water (4×1,200 cc). The aqueous phase thus obtained is extracted with isopropyl ether (8×600 cc). The ether phase thus obtained is washed with water (2×50 cc), dried over sodium sulphate, and then concentrated to dryness. 4-Hydroxy-2,4,6-trimethyl-2,5-cyclohexadienone (24.2 g) is thus obtained, the characteristics of which are as follows:

| | |
|---|---|
| m.p. | 41° C. |
| composition: 4-hydroxy-2,4,6-trimethyl-2,5-cyclohexadienone: | 95% |
| 2,4,6-trimethylphenol: | 1% |

EXAMPLE 18

In a stainless steel autoclave, the following are introduced:

| | |
|---|---|
| water | 200 cc |
| 4-hydroxy-2,4,6-trimethyl-2,5-cyclohexadienone (obtained in Example 17) | 4.48 g |
| caustic soda | 0.056 g |
| sodium sulphite | 0.2 g. |

The reaction mixture is heated to 200° C. for 10 minutes. After the mixture is cooled, the trimethylhydroquinone which has precipitated is separated by filtration. Determination of the trimethylhydroquinone in the precipitate and in the filtrate shows that 3.9 g of trimethylhydroquinone are obtained. The yield is 91% relative to the 4-hydroxy-2,4,6-trimethyl-2,5-cyclohexadienone used.

EXAMPLE 19

The procedure is carried out in the same apparatus as that used in Example 9. The following are introduced:

| | |
|---|---|
| methyl tert.-butyl ether | 200 cc |
| 2,4,6-trimethyl phenol | 13.6 g (100 mmoles) |
| sodium bicarbonate | 16.8 g (200 mmoles) |

The mixture is stirred at a speed of 1000 rpm. With the reaction mixture maintained at 40° C. a steady stream of gaseous chlorine is passed in, in the course of 25 minutes. The total quantity of chlorine used up is. 110 mmoles.

Water (200 cc) is then added rapidly, and stirring is continued for 30 minutes at 40° C. After decantation, the aqueous layer is extracted with methylene chloride (4×50 cc). The organic phases are combined. Analysis of the organic phase by gas-liquid chromatography shows that:
the conversion ratio of 2,4,6-trimethylphenol is 98% the yield of 4-hydroxy-2,4,6-trimethyl-2,5-cyclohexadienone is 85%.

EXAMPLE 20

The procedure is carried out in the same apparatus as that used in Example 9. The following are introduced:

| methyl tert.-butyl ether | 200 cc |
| 2,4,6-trimethylphenol | 13.6 g (100 mmoles) |
| sodium bicarbonate | 16.8 g (200 mmoles) |
| water | 200 cc. |

The mixture is stirred at a speed of 1000 rpm. With the reaction mixture maintained at 25° C., a steady stream of gaseous chlorine is passed in, in the course of 24 minutes. The quantity of chlorine used up is 110 mmoles.

The stirring is continued for 30 minutes at 40° C. After decantation, the aqueous layer is extracted with methylene chloride (4×50 cc). The organic phases are combined. Analysis of the organic phase by gas-liquid chromatography shows that:
the conversion ratio of 2,4,6-trimethylphenol is 99.6%
the yield of 4-hydroxy-2,4,6-trimethyl-2,5-cyclohexadienone is 89.8%.

EXAMPLE 21

The procedure is carried out in the same apparatus as that used in Example 9. The following are introduced:

| methyl tert.-butyl ether | 200 cc |
| 2,4,6-trimethylphenol | 13.6 g (100 mmoles) |
| water | 200 cc. |

The mixture is stirred at a speed of 1000 rpm. With the reaction mixture maintained at 25° C., a steady stream of gaseous chlorine is passed in, in the course of 25 minutes. The quantity of chlorine used up is 110 mmoles.

The stirring is continued for 30 minutes at 40° C. After decantation, the aqueous layer is extracted with methylene chloride (4×50 cc). The organic phases are combined. Analysis of the organic phase by gas-liquid chromatography shows that:
the conversion ratio of 2,4,6-trimethylphenol is 98.1%
the yield of 4-hydroxy-2,4,6-trimethyl-2,5-cyclohexadienone is 90.8%.

EXAMPLE 22

The procedure is carried out in the same apparatus as that used in Example 9. The following are introduced:

| methyl tert.-butyl ether | 200 cc |
| 2,4,6-trimethylphenol | 13.6 g (100 mmoles) |

The mixture is stirred at a speed of 1000 rpm. With the reaction mixture maintained at 20° C., a steady stream of gaseous chlorine is passed in, in the course of 30 minutes. The quantity of chlorine used up is 110 mmoles. Analysis shows that this chlorine has been taken up completely.

Water (200 cc) containing sodium bicarbonate (16.8 g, 200 mmoles) is then added rapidly, and stirring is then continued for 30 minutes at 40° C. After decantation, the aqueous layer is extracted with methyl tert.-butyl ether (4×50 cc). The organic phases are combined. Analysis of the organic phase by gas-liquid chromatography shows that:
the conversion ratio of 2,4,6-trimethylphenol is 80.4%
the yield of 4-hydroxy-2,4,6-trimethyl-2,5-cyclohexadienone is 68.5%.

EXAMPLE 23

The procedure is carried out in the same apparatus as that used in Example 9. The following are introduced:

| methyl tert.-butyl ether | 150 cc |
| 2,4,6-trimethylphenol | 20.4 g (150 mmoles) |
| sodium bicarbonate | 25.2 g (300 mmoles) |
| water | 15 cc. |

The mixture is stirred at a speed of 1000 rpm. With the reaction mixture maintained at 25° C., a steady stream of gaseous chlorine is passed in, in the course of 26 minutes. The total quantity of chlorine used up is 165 mmoles.

Water (135 cc) is then added rapidly, and stirring is continued for 30 minutes at 40° C. After decantation, the aqueous layer is extracted with methyl tert.-butyl ether (4×50 cc). The organic phases are combined. Analysis by gas-liquid chromatography shows that:
the conversion ratio of 2,4,6-trimethylphenol is 98.5%
the yield of 4-hydroxy-2,4,6-trimethyl-2,5-cyclohexadienone is 84.5%.

EXAMPLE 24

The procedure is carried out in the same apparatus as that used in Example 9. The following are introduced:

| methyl tert.-butyl ether | 200 cc |
| 2,4,6-trimethylphenol | 13.6 g (100 mmoles) |
| sodium bicarbonate | 16.8 g (200 mmoles) |
| water | 20 cc. |

The mixture is stirred at a speed of 1000 rpm. With the reaction mixture maintained at 50° C., a steady stream of gaseous chlorine is passed in, in the course of 28 minutes. The total quantity of chlorine used up is 110 mmoles.

Water (180 cc) is then added rapidly, and stirring is continued for 30 minutes at 40° C. After decantation, the aqueous layer is extracted with methyl tert.-butyl ether (4×50 cc). The organic phases are combined. Analysis by gas-liquid chromatography shows that:
the conversion ratio of 2,4,6-trimethylphenol is 96%
the yield of 4-hydroxy-2,4,6-trimethyl-2,5-cyclohexadienone is 85%.

EXAMPLE 25

The procedure is carried out in the same apparatus as that used in Example 9. The following are introduced:

| ethyl acetate | 200 cc |
| 2,4,6-trimethylphenol | 13.6 g (100 mmoles) |
| sodium bicarbonate | 16.8 g (200 mmoles). |

The mixture is stirred at a speed of 1000 rpm. With the reaction mixture maintained at 0° C., a steady stream of gaseous chlorine is passed in, in the course of 24 minutes. The total quantity of chlorine used up is 100 mmoles.

Water (200 cc) is then added rapidly, and the stirring is continued for 3 hours at 25° C. After decantation, the aqueous layer is extracted with methylene chloride (4×50 cc). The organic phases are combined. Analysis of the organic phase by gas-liquid chromatography shows that:

the conversion ratio of 2,4,6-trimethylphenol is 81.5%
the yield of 4-hydroxy-2,4,6-trimethyl-2,5-cyclohexadienone is 74%.

EXAMPLE 26

The procedure is carried out in the same apparatus as that used in Example 9. The following are introduced:

| methylcyclohexane | 200 cc |
| 2,4,6-trimethylphenol | 13.6 g (100 mmoles) |
| sodium bicarbonate | 16.8 g (200 mmoles) |

The mixture is stirred at a speed of 1000 rpm. With the reaction mixture maintained at 25° C., a steady stream of gaseous chlorine is passed in, in the course of 26 minutes. The total quantity of chlorine used up is 98.5 mmoles.

Water (200 cc) is then added rapidly, and the stirring is continued for 30 minutes at 25° C. After decantation, the aqueous layer is extracted with methylene chloride (4×50 cc). The organic phases are combined. Analysis of the organic phase by gas-liquid chromatography shows that:

the conversion ratio of 2,4,6-trimethylphenol is 95.5%
the yield of 4-hydroxy-2,4,6-trimethyl-2,5-cyclohexadienone is 64.5%.

We claim:

1. Process for the preparation of 4-hydroxy-2,4,6-trimethyl-2,5-cyclohexadienone which comprises reacting 2,4,6-trimethylphenol with chlorine in an inert organic solvent selected from the class consisting of aliphatic and cycloaliphatic hydrocarbons which may be halogenated, aliphatic carboxylic acid esters and ethers, in the presence of an alkali metal hydroxide, bicarbonate or carbonate, and then hydrolysing the chlorination product with water, with or without an inorganic base, at a pH of 0 to 10.

2. Process for the preparation of 4-hydroxy-2,4,6-trimethyl-2,5-cyclohexadienone which comprises reacting 2,4,6-trimethylphenol with chlorine and water in an inert organic solvent selected from the class consisting of aliphatic and cycloaliphatic hydrocarbons, which may be halogenated, aliphatic carboxylic acid esters and ethers in the presence of an alkali metal hydroxide, carbonate or bicarbonate at a pH of 0 to 10.

3. Process according to claim 1, in which the organic solvent used is not miscible with water and the 4-Hydroxy-2,4,6-trimethyl-2,5-cyclohexadienone is isolated after extraction of the organic phase with water.

4. Process according to claim 2, in which the organic solvent used is not miscible with water and the 4-hydroxy-2,4,6-trimethyl-2,5-cyclohexadienone is isolated after extraction of the organic phase with water.

* * * * *